US006926890B2

(12) United States Patent
Vogelstein et al.

(10) Patent No.: US 6,926,890 B2
(45) Date of Patent: *Aug. 9, 2005

(54) NON-INVASIVE APPROACH FOR ASSESSING TUMORS IN LIVING ANIMALS

(76) Inventors: Bert Vogelstein, 3700 Breton Way, Baltimore, MD (US) 21208; Kenneth W. Kinzler, 1403 Halkirk Way, Bel Air, MD (US) 21015; Le-Ming Shih, 5208 Springlakes Way, Baltimore, MD (US) 21212

(*) Notice: Subject to any disclaimer, the term of this patent is extended or adjusted under 35 U.S.C. 154(b) by 405 days.

This patent is subject to a terminal disclaimer.

(21) Appl. No.: 10/114,030

(22) Filed: Apr. 3, 2002

(65) Prior Publication Data

US 2002/0119099 A1 Aug. 29, 2002

Related U.S. Application Data

(63) Continuation of application No. 09/517,740, filed on Mar. 3, 2000, now Pat. No. 6,419,896.

(51) Int. Cl.[7] .................. A01N 63/00; A61K 49/00; A61K 35/22; C12P 21/06
(52) U.S. Cl. .................. 424/93.2; 424/9.1; 424/545; 435/69.1
(58) Field of Search .................. 424/545, 9.1–9.2, 424/93.1–93.2, 277.1; 435/69.1

(56) References Cited

U.S. PATENT DOCUMENTS 6,419,896 B1 * 7/2002 Vogelstein et al. .......... 424/9.2

OTHER PUBLICATIONS

Marine et al., "Assessment of bystander effect potency produced by intratumoral implantation of HSVtk–expressing cells using surrogate marker secretion to monitor tumor growth kinetics", *Gene Therapy*, (1995), 2, pp. 665–669.

Pesce et al., "Human Lactic Dehydrogenase as a Marker for Human Tumor Cells Grown in Athymic Mice", *Cancer Research*, 37, pp. 1998–2003, Jul. 1977.

Coimbra et al., *Braz. J. Med. Biol. Res.*, vol. 17, 1984.

Umovitz et al., *Trends Biotech. Sci.*, vol. 14, 1996.

Iles et al., *Prenat Diagn.*, vol. 18, 1998, abstract only.

* cited by examiner

*Primary Examiner*—Gary Nickol
(74) *Attorney, Agent, or Firm*—Banner & Witcoff, Ltd.

(57) ABSTRACT

A means for following the growth of experimental neoplasms involves administering recombinant tumor cells containing an expression construct encoding a secretable marker to an experimental animal and measuring secreted marker in the urine of animals bearing tumors formed by such recombinant tumor cells. Urinary marker levels are quantitatively related to tumor loads. Urinary marker can be detected before tumors are grossly visible or clinically apparent. Marker levels decrease following surgical excision or chemotherapeutic treatment, with an estimated half-life of 11 hours. This approach is applicable to the study of many experimental tumor systems.

18 Claims, 11 Drawing Sheets

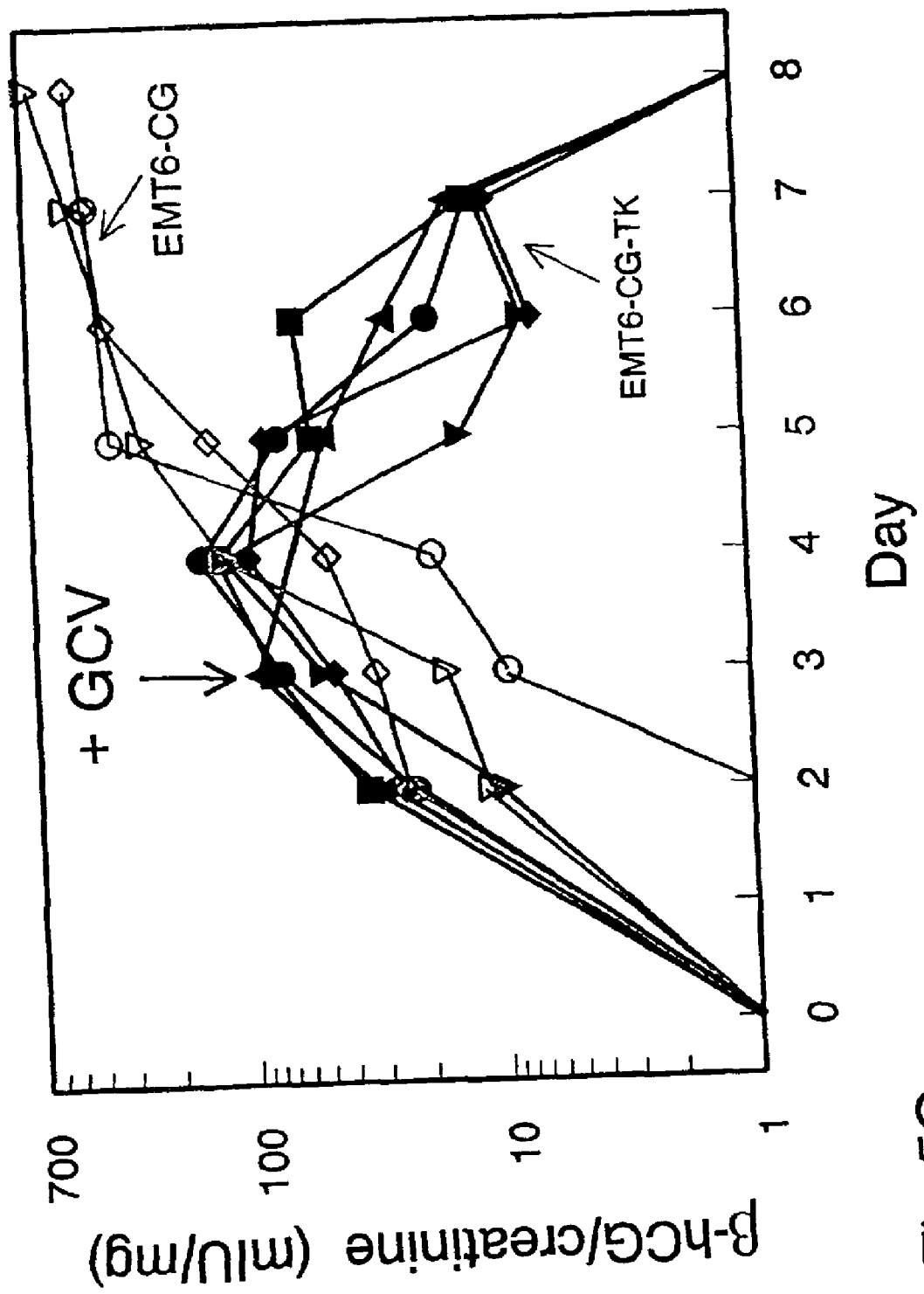

SEQUENCE LISTING

<160> NUMBER OF SEQ ID NOS: 2

<210> SEQ ID NO 1
<211> LENGTH: 38
<212> TYPE: DNA
<213> ORGANISM: Homo sapiens

<400> SEQUENCE: 1

```
                                  -continued tgtgctctag atcatgacca aggatggaga tgttccag                              38

<210> SEQ ID NO 2
<211> LENGTH: 31
<212> TYPE: DNA
<213> ORGANISM: homo sapiens

<400> SEQUENCE: 2
gcacagtcta gattattgtg ggaggatcgg g                                     31
```

NON-INVASIVE APPROACH FOR ASSESSING TUMORS IN LIVING ANIMALS

This is a Continuation application of parent application Ser. No. 09/517,740, filed Mar. 3, 2000, U.S. Pat. No. 6,419,896.

The U.S. Government has a paid-up license in this invention and the right in limited circumstances to require the patent owner to license others on reasonable terms as provided for by the terms of Grant Nos. CA 57345, CA 43460, and CA 62924 awarded by the National Institutes of Health.

BACKGROUND OF THE INVENTION

There is no tool more essential to cancer research than the experimental tumor. Every therapeutic and preventative strategy employs such tumors, and tumors growing in animals are instrumental to basic studies of cancer biology. Many experimental tumors are injected subcutaneously because subsequent growth can be followed visually. However, it is often preferable to have tumors grow internally. Such internal growths more closely mimic the environment of naturally occurring tumors, because host factors (blood supply, immune recognition and destruction, extracellular matrix, etc.) are far different at internal sites than in the skin. Metastasis, a defining feature of malignancy, cannot be assessed through observation of the skin. Moreover, the size of subcutaneous tumors often does not reflect the true tumor load, as the volume composed of stroma, necrosis, and scar tissue cannot be distinguished from that occupied by neoplastic cells.

For these reasons, internal tumors have also been widely used for studies of tumor biology. However, the presence of internal tumors is generally apparent only when symptoms develop, which generally occurs quite late during tumorigenesis. Surgical approaches to detect smaller internal tumors can be useful, but anesthetics and surgical manipulation can disturb the natural course of tumorigenesis and introduce other variables into the analysis. Human lactic dehydrogenase and $\alpha$-1-antitrypsin have been proposed as serum markers in xenograft-nude mice tumor models. However, the repetitive anesthesia and blood collections required for these approaches have hampered their widespread use.

In addition, mice with internal tumors are generally sacrificed at the end of an experimental protocol to determine how the tumors have responded. Only a single time point can be assessed using this approach, and multiple mice must be studied to minimize the effects of tumor and host heterogeneity. Imaging techniques provide a way of following tumor growth in situ, but are only applicable to rather large tumors.

To overcome the problems noted above, there is a need in the art for a system for monitoring internal tumor growth that would (i) provide a quantitative measure of neoplastic cell content, (ii) be cost-effective and simple to implement, and (iii) be broadly applicable to diverse tumor types and hosts.

SUMMARY OF THE INVENTION

It is an object of the present invention to provide a method for monitoring growth of an experimentally induced tumor within an animal body.

It is another object of the present invention to provide a device for collecting urine from a small mammal.

It is another object of the present invention to provide a method for collecting urine from a small mammal.

These and other objects of the invention are provided by one or more of the embodiments described below.

One embodiment of the invention provides a method for monitoring growth of tumor cells within an animal body. A recombinant tumor cell which comprises an expression construct encoding a secretable exogenous marker protein is administered to an animal. Urine is collected from the animal and secretable exogenous marker protein in the urine is measured. Secretable exogenous marker protein in the urine is proportional to the number of viable tumor cells in the animal.

Another embodiment of the invention provides a device for collecting urine from a small mammal. The device has a floor comprising a plurality of liquid-impermeable wells for deposition of urine by a small mammal. The device also has one or more walls enclosing at least a portion of the plurality of wells. The walls of the device are of sufficient height to inhibit or prevent escape of the small mammal. The floor of the device comprises sufficient wells within the walls so that at least 50% of the wells which are occupied by urine are not also occupied by feces after a period of time sufficient for 90% of a population of healthy said small mammals to have urinated.

Yet another embodiment of the invention provides another device for collecting urine from a small mammal. The device has a floor comprising a plurality of liquid-impermeable wells for deposition of urine by a small mammal. The device also has one or more walls enclosing at least a portion of the plurality of wells. A small mammal is on the floor and within the walls. The walls of the device are of sufficient height to inhibit or prevent escape of the small mammal.

Still another embodiment of the invention provides a method for collecting urine from a small mammal. A small mammal is placed in a device comprising a floor and one or more walls. The floor of the device comprises a plurality of liquid-impermeable wells for deposition of urine by a small mammal and one or more walls enclosing at least a portion of the plurality of wells. The walls of the device are of sufficient height to inhibit or prevent escape of the small mammal.

The invention thus provides the art with non-invasive methods and devices for frequently monitoring a biochemical marker in the urine of experimental animals.

BRIEF DESCRIPTION OF THE DRAWINGS

FIG. 5C. Urinary β-hCG levels before and after ganciclovir (GCV) treatment of intraperitoneal tumors. Five Balb/c mice were injected intraperitoneally with $4 \times 10^6$ EMT6-CG-TK cells (black symbols). They received a four-day course of ganciclovir (150 mg/kg/day), administered intraperitoneally beginning three days after tumor cell injection. The β-hCG levels began to decline one day after the start of ganciclovir treatment. In contrast, control EMT6-CG tumors (gray symbols) did not respond to ganciclovir, as indicated by the progressive rise in urinary β-hCG.

DETAILED DESCRIPTION OF THE INVENTION

Figure 1:
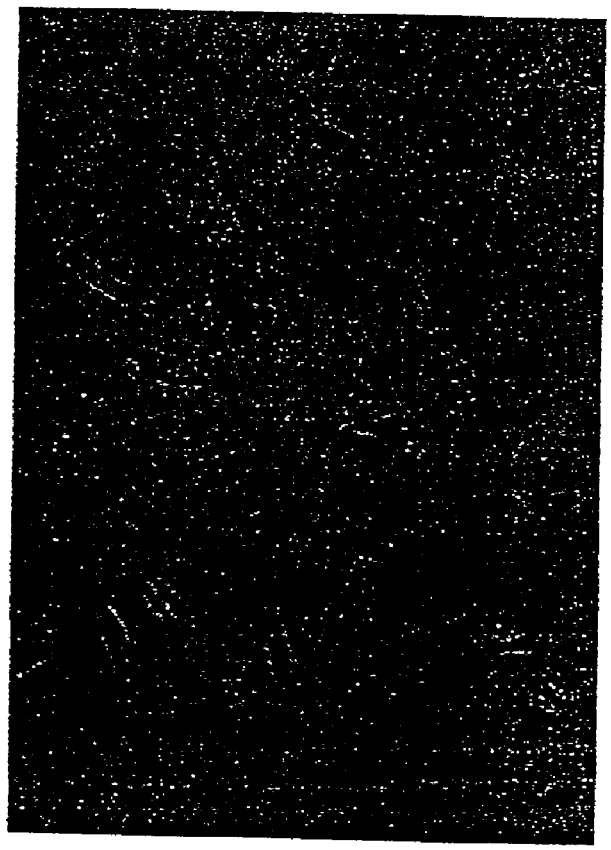
FIG. 1A. Immunostaining of $\beta$-hCG in EMT6-CG cells. EMT6-CG cells stained uniformly with an anti-$\beta$-hCG antibody, with immunoreactivity confined to the cytoplasm.
FIG. 1B. Immunostaining of $\beta$-hCG in EMT6-CG cells. No staining was apparent when the primary antibody was omitted in the staining reaction.
Figure 1:
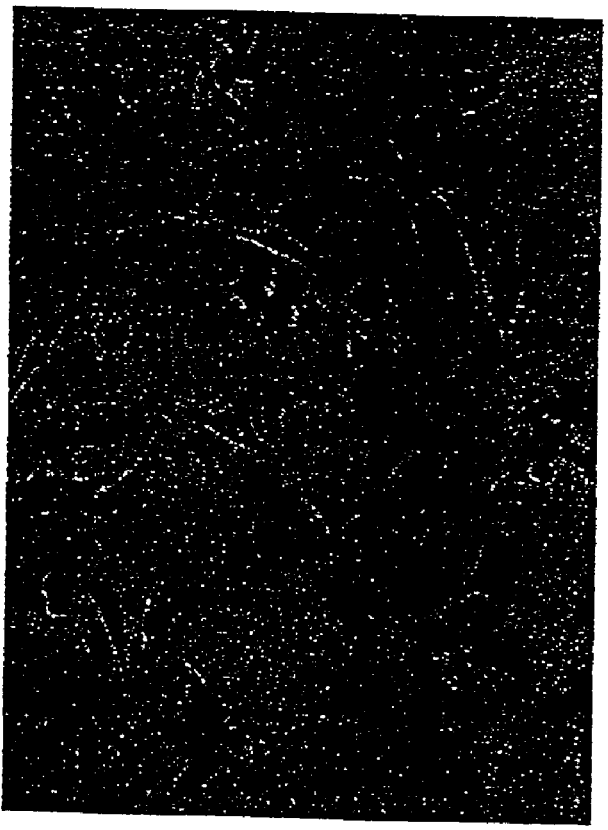

It is a discovery of the present invention that the growth of an internal experimental tumor within an animal body can be monitored frequently without invasive methods or complex instrumentation by monitoring in the urine a gene product secreted by the tumor. The response of experimental tumors to potential therapeutic agents can thus be easily monitored, even when the tumors are still relatively small.

Tumors can be experimentally induced in animals by injecting recombinant tumor cells which express an easily detectable, secreted, exogenous protein into the animals. The recombinant tumor cells continue to express the exogenous protein after transplantation. The inventors have found that the level of the exogenous protein in the urine is proportional to the number of viable recombinant tumor cells in the animals. Measurement of urinary exogenous protein secreted from recombinant tumor cells thus provides a useful system for following and quantifying experimental tumor growth in a non-invasive manner.

By monitoring the exogenous protein in the urine, the extent of experimental tumor growth can be determined without repeated anesthesia and invasive blood collections which may disrupt the natural course of tumorigenesis and may introduce additional variables into the analysis. Urine can be non-invasively collected at will, e.g., once a day or at multiple time intervals during a single day, such as every 1, 2, 3, 4, 6, 8, or 12 hours.

The ability to know which animals have internal experimental tumors prior to treatment, as well as the precise tumor load in each individual animal, simplifies experimental designs. Moreover, smaller numbers of animals are required for each experiment, and data defining the growth kinetics of internal tumors, rather than just the final endpoint of treatment, can be obtained.

Recombinant Tumor Cells

Recombinant tumor cells according to the invention may secrete any exogenous marker protein which can be detected in the urine. Such markers include, but are not limited to, proteins such as β-hCG, prostate specific antigen (PSA), cortisol, thyroxin, parathyroid hormone, insulin, glucagon, vasoactive intestinal peptide, vasopressin, estrogen, progesterone, testosterone, and growth hormone. β-hCG is a glycoprotein hormone secreted by syncytiotrophoblasts during pregnancy and in gestational trophoblastic tumors, and it can be sensitively detected in urine. Biologically active hCG is composed of two subunits, α and β, joined noncovalently. While the α-subunit is similar to that of several pituitary hormones, the β-subunit is unique to hCG. Thus it can be uniquely identified even in the presence of other hormones. Furthermore, the concentration of β-hCG in urine is highly correlated with its concentration in serum.

Recombinant tumor cells of the present invention can be made by transfecting tumor cells with an expression construct which expresses the secretable exogenous marker protein. Recombinant tumor cells can be syngeneic (from genetically identical animals), allogeneic (from genetically distinct animals), or xenogeneic (from a different species) to the animal host. Tumor cells suitable for transfection include both trophoblastic and nontrophoblastic tumor cells which can be obtained from primary tumors as well as tumor cell lines. Suitable tumor cells include B16-F10 melanoma cells, EMT6 mouse mammary carcinoma cells, colon cancer cell lines HCT116, DLD1, HT29, Caco2, SW837, SW480, and RKO, breast cancer cell lines 21-PT, 21-MT, MDA-468, SK-BR3, and BT-474, A549 lung cancer cells, and H392 glioblastoma cells. It is essential that the tumor cells chosen are tumorigenic in the animal model chosen.

Any appropriate transfection method known in the art can be used to introduce a secretable marker expression construct into a tumor cell, including, but not limited to, non-liposomal methods such as a method utilizing the FuGene 6™ reagent (Boehringer Mannheim, Indianapolis, Ind.), calcium co-precipitation, electroporation, or liposomal methods such as lipofection using cationic lipids. Expression constructs preferably include a promoter, such as a standard CMV promoter/enhancer, the SV40 early or late promoter, the Rous Sarcoma Virus (RSV) promoter, eukaryotic promoters such as the β-actin promoter, the GADPH promoter, or the metallothionein promoter. Suitable viral or plasmid vectors known in the art can be used, such as the tgCMV/HyTK vector, pBS185, pBS226, or pSF1. If desired, the expression construct can contain a selectable genetic marker, such as an antibiotic resistance gene, so that successful transfectants can be selected in media containing an appropriate antibiotic such as hygromycin, geneticin, or mycophenolic acid. Alternatively, other methods can be used to identify genetic marker-expressing cells, as is known in the art. These include immunological or enzyme assays, for example.

Preferably, recombinant tumor cells express the secretable exogenous marker protein constitutively. Levels of exogenous marker protein secretion by individual clones of recombinant tumor cells can be conveniently assessed through measurements of the secretable exogenous marker protein in the cell culture medium, as described below (see, e.g., Example 3). Though extraordinarily high levels of production should not be required for most applications, higher expression levels might be useful when detection of very small numbers of tumor cells or of tumors in poorly vascularized compartments is desired. It is well within the skill in the art to select suitable expression vectors for achieving higher levels of expression.

Administration of Recombinant Tumor Cells to Animals

Recombinant tumor cells which express the secretable exogenous marker protein can be administered to any animal selected as a convenient model, such as a mouse, shrew, mole, gerbil, squirrel, chipmunk, vole, rat, hamster, guinea pig, rabbit, monkey, chimpanzee, goat, horse, cow, or sheep, to provide the animal with a tumor burden. Optionally, the animal may be athymic, such as a nude mouse. Recombinant tumor cells can be administered to animals by any method known in the art. Such methods include, but are not limited to, subcutaneous, intravenous, intraperitoneal, intrasplenic, intra-bladder, and intracranial injection, injection under the renal capsule, and injection directly into the bowel wall. Typically the number of cells injected ranges from $10^4$ to $10^6$ cells in a volume of about 100 µl to about 200 µl. The number and volume of cells administered to an animal can be varied, depending on the type of tumor cells used, the particular injection site, the size of the animal, and the size and time frame of the desired resultant tumor. For example, $10^2$, $10^3$, $10^5$, $10^7$, $10^8$, $10^9$, or $10^{10}$ cells in a volume of at least about 25 µl to about 500 µl, 200 µl to 1 ml, or 500 µl to 2 ml can be administered to an animal to induce experimental tumors.

Measurements of Markers to Monitor Tumor Growth

Secretable exogenous marker proteins can be measured using an immunoradiometric assay, such as the β-hCG MAIAclone kit system taught in Example 3. In addition to immunoradiometric assays, any other appropriate assay known in the art for measuring the marker, including chemiluminescent immunoassays and enzyme-linked colorimetric immunoassays, can be used.

Measurements of metabolites such as creatinine can be used to normalize secretable exogenous marker protein measurements to control for any changes in urine output that might occur if the animals become unhealthy. Creatinine is secreted into the urine at nearly constant rates independent of fluid balance. Other metabolites with the same characteristics as creatinine also can be used to normalize secretable exogenous marker protein measurements. Creatinine can be measured using any suitable assay known in the art (see e.g., Example 3). Measurement of secretable exogenous marker protein levels in sera also can be used to confirm that measurements of the secretable exogenous marker protein in urine are an accurate reflection of secretable exogenous marker protein production by experimentally induced tumors. Sera can be collected daily and urine can be collected at several different time points during the day.

The present invention can be used to monitor growth of experimentally induced internal tumors in various organs such as brain, liver, lungs, kidney, spleen, breast, colon, or bladder. After recombinant tumor cells are administered to animals, their urine can be collected at regular time intervals and assayed for the presence and or quantity of the secretable exogenous marker protein.

Urine from the tumor-bearing animals can be collected using traditional metabolic cages. However, commercially available cages are large, expensive, and ill-suited for urine collections in small mammals such as mice, shrews, moles, gerbils, squirrels, chipmunks, voles, prairie dogs, rats, or hamsters. Preferably a urine collection device as described in detail below is used to collect urine for secretable exogenous marker protein assays.

Urine Collection Device

Urine collection devices have a floor and plurality of liquid impermeable wells within which a small mammal can deposit at least about 25 µl to about 250 µl of urine. Preferably, there are a sufficient number of wells such that at least about 50%, 75%, or 95% of the wells containing urine do not also contain feces after a period of time sufficient for 90% of a population of the small mammals which are healthy to have urinated. Walls of sufficient height to prevent escape of the small mammal enclose at least a portion of the plurality of wells.

A 96-well, plastic PCR plate and a pipette tip box can be used to make a urine collection device. Multiple plates with liquid impermeable wells can be combined to increase the size of the urine collection device such that urine can be collected from small mammals larger than mice, including but not limited to, shrews, moles, gerbils, squirrels, chipmunks, voles, prairie dogs, rats, hamsters, guinea pigs, or rabbits. Any suitable plastic plates known in the art can be used to comprise the floor of the urine collection device, including, but not limited to, 12, 24, 48, 72, and 96-well plates or strips or a combination thereof.

Any suitable material can be used to comprise the walls of the urine collection device so long as the walls are of sufficient width, height, and strength to prevent the escape of the small mammal. In addition, the dimensions of the device should be sufficient to permit a mammal placed in the device to stand, turn around, walk, and excrete. Examples of suitable materials include, but are not limited to, plastic, plexiglass, glass, wood, or metal.

After tumor induction, the small mammal is placed in the urine collection device of the present invention for a sufficient time such that 90% of a population of healthy small mammals would have urinated, (e.g., at least 3 to about 6 hours for mice). The small mammal also is housed in the urine collection device for a time sufficient for it to produce a urine sample of appropriate volume, preferably at least about 25 µl to about 250 µl. The small mammal can be allowed to excrete for a time period such that a substantial proportion of the wells that contain urine do not also contain feces. Preferably at least about 50%, 75%, or 95% of the wells containing excretions contain only urine.

Urine samples can be collected once a day or at multiple time intervals throughout one or more days (e.g. every 1, 2, 3, 4, 6, 8, or 12 hours). Urine can be withdrawn from the device and assayed for secreted exogenous marker protein and normalization metabolite levels immediately post-collection or withdrawn from the device and frozen at a temperature of at least about −20° C. to at least about −80° C. until it can be assayed.

Testing the Effect of Therapeutic Agents or Potential Therapeutic Agents

Measurements of secreted exogenous marker protein levels in the urine permit determination of the precise tumor load the animal is carrying over time, and consequently, effectiveness of a therapeutic agent or potential therapeutic agent against internal tumor growth. Therapeutic agents with known anti-tumor effects, such as cytosine arbinoside, fluorouracil, methotrexate or aminopterin, an anthracycline, mitomycin C, vinca alkaloids, demecolcine, etoposide, mithramycin, or an antitumor alkylating agent such as chlorambucil or malphalan can be tested for their efficacy against particular tumor types and stages. Potential therapeutic agents which can be tested include agents which are known in the art to have a pharmacological activity or can be compounds whose pharmacological activity is unknown. Compounds which can be tested include substances which are naturally occurring or which are designed in the laboratory, including members of small molecule libraries. They can be isolated from microorganisms, animals, or plants, or be produced recombinantly or by chemical synthesis. They can be purified or in mixtures in extracts.

A therapeutic agent or potential therapeutic agent can be administered to an animal by any means known in the art, such as orally or by injection, and either before, after or concomitant with administration of recombinant tumor cells. Secretable exogenous marker protein levels in the urine of the animal are then measured at various time points. A decrease in secretable exogenous marker protein levels in the urine identifies the therapeutic or potential therapeutic agent as potentially useful for treating tumors.

The present invention provides a simple and reliable method to monitor the growth of experimentally induced tumors over multiple time intervals, as well as a device useful for regular collection of urine samples from small mammals. A more complete understanding of the present invention can be obtained by reference to the following specific examples. These examples are provided for purposes of illustration only and are not intended to limit the scope of the invention.

EXAMPLE 1

Materials and Methods

B 16-F10 (mouse melanoma cell line), EMT6 (mouse mammary carcinoma cell line), and SW480 (human colon carcinoma cell line) cells were obtained from the American Type Culture Collection. B16 and EMT6 cells were maintained in DMEM growth medium (Life Technologies, Gaithersburg, Md.), and SW480 cells were cultivated in McCoy's 5A medium (Life Technologies). Media was supplemented with 10% fetal bovine serum (HyClone, Logan, Utah), 100 U/ml of penicillin, and 100 µg/ml of streptomycin.

To generate a β-hCG expression vector, a hCG cDNA fragment (534 bp) was amplified via PCR from human placental cDNA (Clontech, Palo Alto, Calif.), using the primers
5'-TGTGCTCTAGATCATGACCAAGGATGGAGAT GTTCCAG-3' (SEQ ID NO:1) and
5'-GCACAGTCTAGATTATTGTGGGAGGATCGGG-3' (SEQ ID NO: 2). The PCR product was sequenced to confirm that it was mutation-free and cloned through several steps into the pCIneo expression vector (Clontech, Palo Alto, Calif.), generating pCI-hCG. The tgCMV/HyTK vector, containing a herpes simplex virus thymidine kinase (HSVtk) gene fused to a hygromycin-resistance element, was obtained from Targeted Genetics Co. (Seattle, Wash.).

EXAMPLE 2

Generation of Recombinant Tumor Cells

Cells of three different cancer cell lines were transfected with the β-hCG expression vector as described below. A total of $2 \times 10^6$ cells were transfected with 9 µg of linearized plasmid DNA using the FuGene 6™ reagent (Boehringer Mannheim, Indianapolis, Ind.) according to the manufacturer's instructions. Approximately 70%, 60%, and 25% of tested clones derived from EMT-6, B16, and SW480 cells, respectively, stained uniformly and intensely with an antibody to β-hCG (FIG. 1).

Transfectants which constitutively expressed β-hCG were maintained in medium supplemented with 10% fetal bovine serum and 2 mg/ml geneticin. EMT6-CG-TK cells, which expressed herpes simplex virus thymidine kinase (TK) as well as β-hCG, were maintained in DMEM with 10% fetal bovine serum, 2 mg/ml geneticin, and 1.5 mg/ml Hygromycin B (Calbiochem, La Jolla, Calif.).

After ten days of selection in geneticin, clones of the recombinant tumor cells were evaluated for expression of β-hCG by immunohistochemistry. The expression of β-hCG in clones exhibiting uniform immunohistochemical staining was verified by analyzing supernatants from clones of the recombinant tumor cells grown in multiwell plates. Recombinant tumor cells transfected with tgCMV/HyTK were selected in hygromycin and tested for ganciclovir sensitivity.

One recombinant tumor cell clone from each cell line was selected for further study (and designated "EMT6-CG", "B16-CG", and "SW480-CG", respectively). Each of these recombinant tumor cell clones secreted substantial levels of β-hCG into the culture medium (35, 24, and 16 mIU/$10^5$ cells, respectively). These lines exhibited morphologies and growth rates indistinguishable from their parent lines both in vitro and in vivo. The expression of β-hCG remained stable for at least six months in culture.

EXAMPLE 3

Urine Collection and Measurement of Urinary β-hCG and Creatinine

Female mice, 10–12 weeks old, were obtained from Harlan (Indianapolis, Ind.). For tail vein injections, $10^5$ B 16-CG cells in 0.1 ml PBS were injected into C57BL/6 mice. For intraperitoneal administration, $2 \times 10^6$ EMT6-CG cells in 0.3 ml PBS were injected intraperitoneally into Balb/c mice. For intrasplenic injection, $10^6$ B16-CG cells in 0.1 ml PBS were injected into the spleens of athymic (nu/nu) mice. For subcutaneous injection, $3 \times 10^6$ B16-CG cells or $8 \times 10^6$ SW480-CG cells in 0.1 ml PBS were injected into subcutaneous tissues adjacent to the lower spine of athymic (nu/nu) mice.

Figure 2:
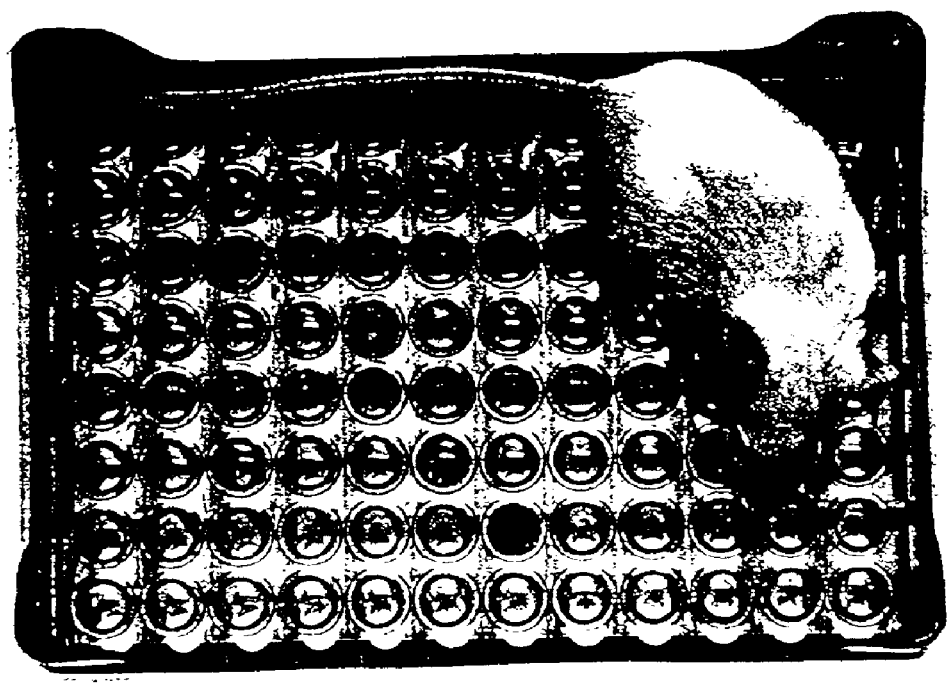
FIG. 2A. Apparatus for mouse urine collection. An individual mouse was placed in a "house" made from a plastic pipette tip box, with a 96-well PCR plate serving as the "floor."
FIG. 2B. Apparatus for mouse urine collection. Urine and fecal specimens were generally found within separate wells a few hours later.
Figure 2:
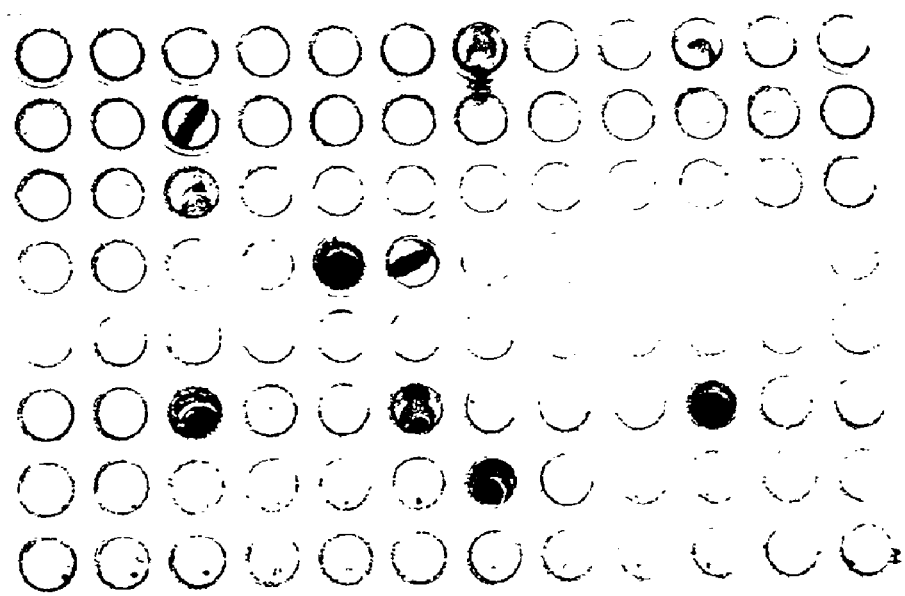
Figure 3A:
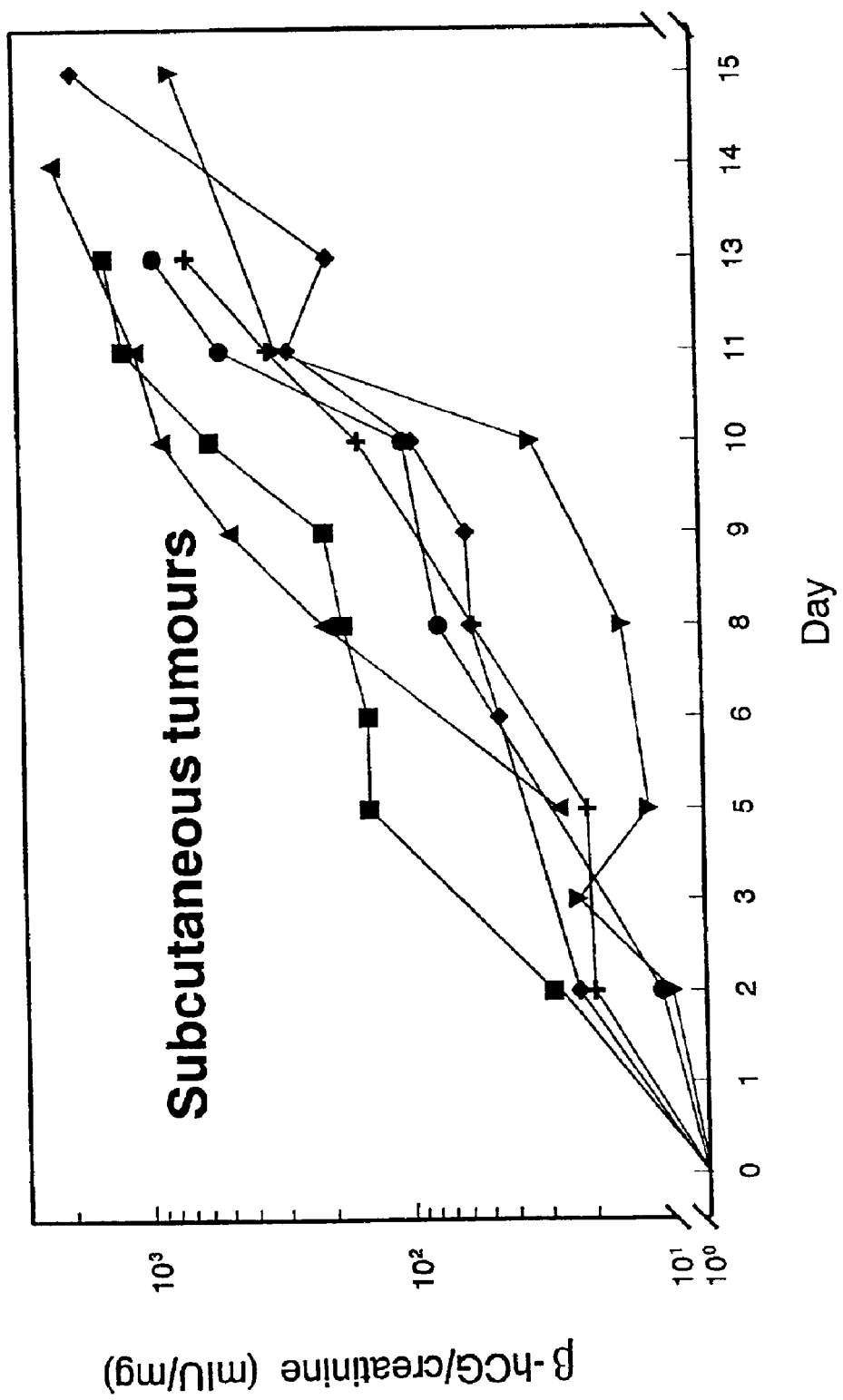
FIG. 3A. Time-course of urinary $\beta$-hCG after tumor cell inoculation. Nude mice with B16-CG tumors introduced by subcutaneous injection of $3\times10^6$ cells.
Figure 3B:
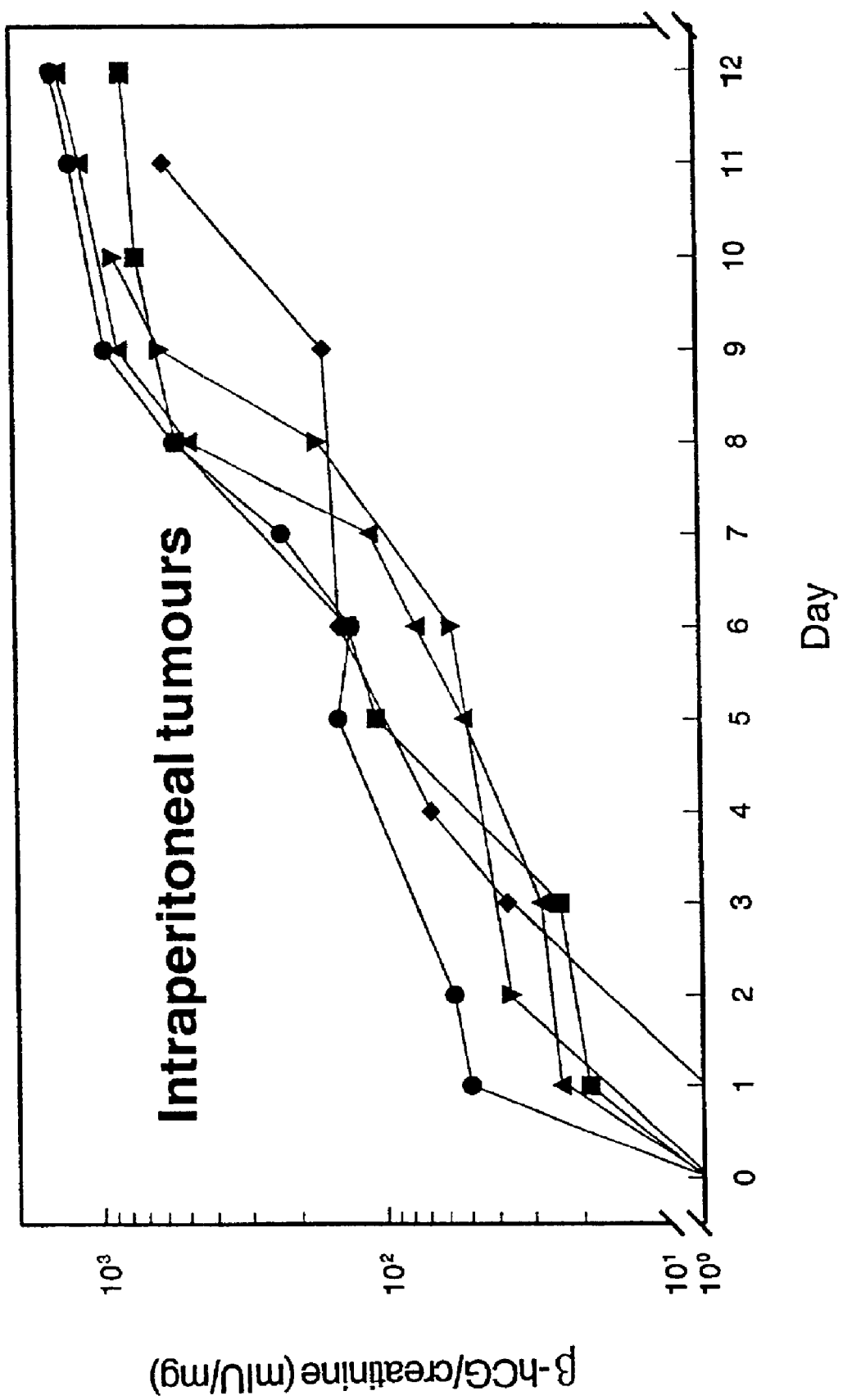
FIG. 3B. Time-course of urinary $\beta$-hCG after tumor cell inoculation. Balb/c mice with EMT6-CG tumors introduced by intraperitoneal injection of $2\times10^6$ cells.
Figure 3C:
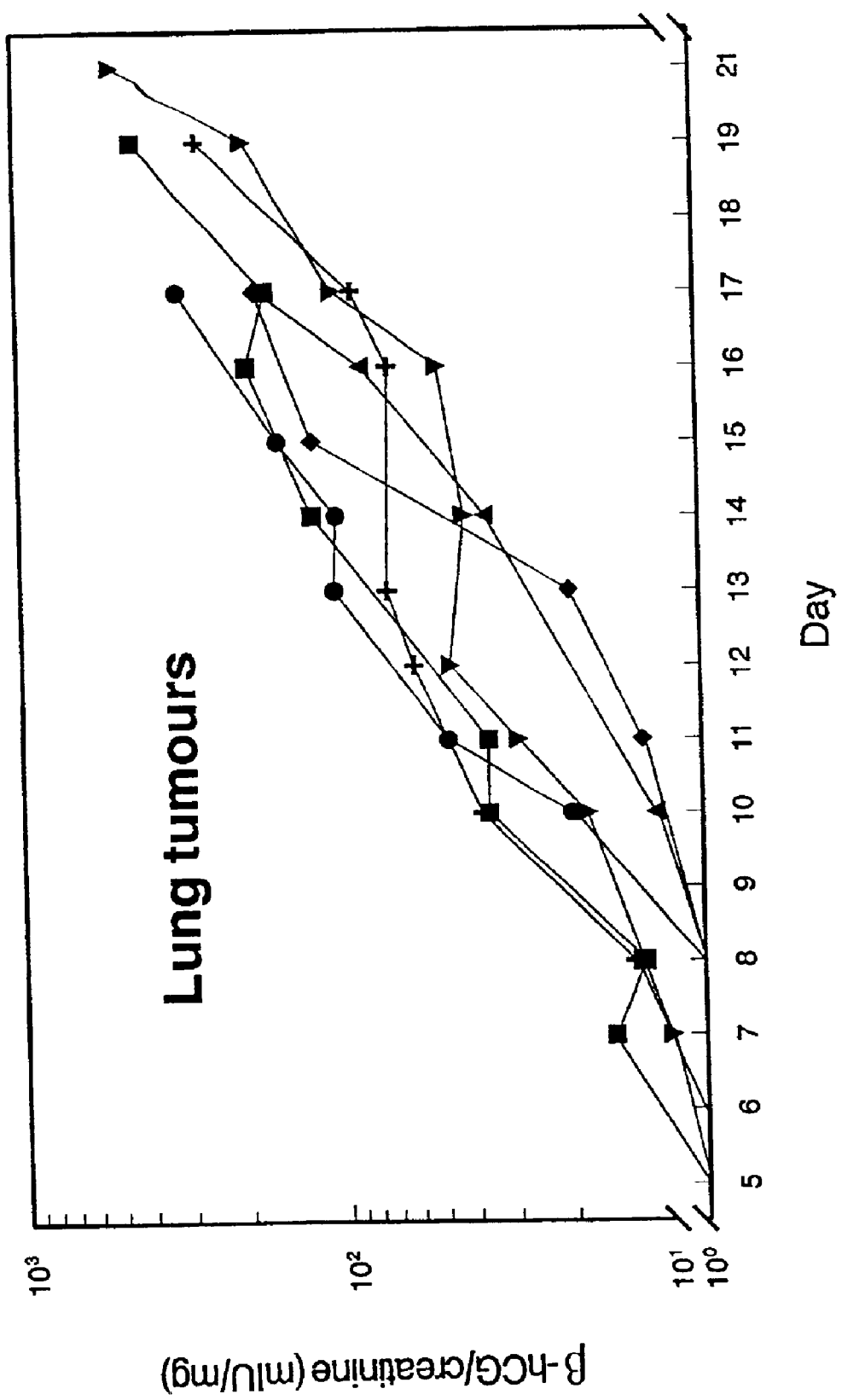
FIG. 3C. Time-course of urinary β-hCG after tumor cell inoculation. C57BL/6 mice with B16-CG tumors in the lungs, introduced by tail vein injection of $10^5$ cells.
Figure 3D:
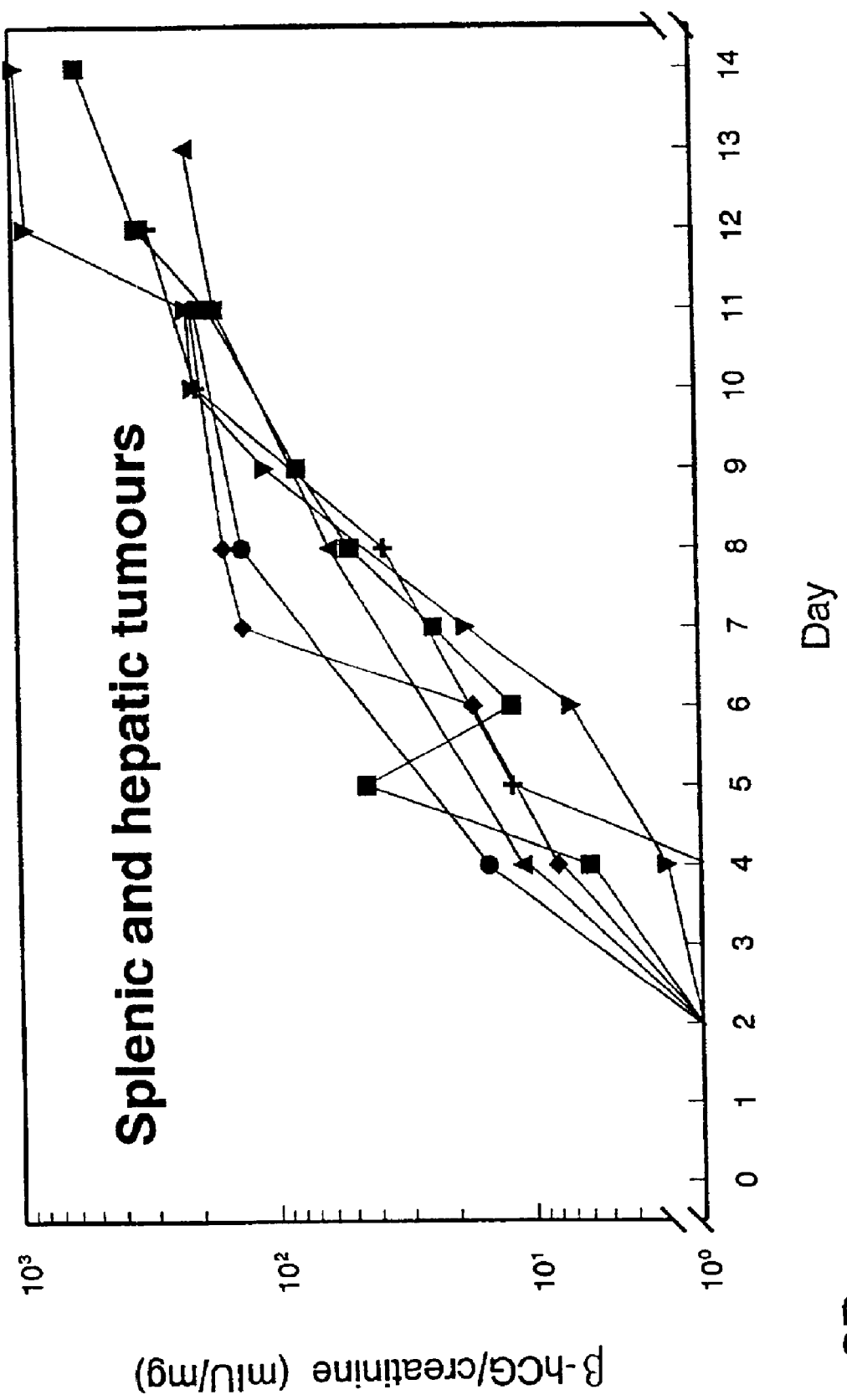
FIG. 3D. Time-course of urinary β-hCG after tumor cell inoculation. Nude mice with splenic and hepatic B16-CG tumors introduced by intrasplenic injection of $10^6$ cells.

Standard laboratory plasticware was reconfigured to form a urine collection device. A "house" was made by placing a 96-well 0.2 ml PCR plate (Research Products International Corp., Mount Prospect, Ill.) on an inverted pipette tip rack inside the box (see FIG. 2). Mice were placed in the "house" and the wells were checked for urine deposition. Within three hours, more than 90% of healthy mice were found to have urinated, with the urine conveniently residing in one or a few wells (FIG. 2B). The only mice that did not urinate within three hours were those which were moribund due to large tumor burdens. Feces were generally found in separate wells, with the probability of feces and urine occupying the same well obeying a Poisson distribution. Mice were then returned to their cages and urine specimens were harvested from the wells and frozen at −20° C. until assayed.

To normalize the measurements to control for any changes in urine output that might occur as mice became unhealthy, the ratios of β-hCG to creatinine, a metabolite which is secreted into the urine at nearly constant rates independent of fluid balance, were also determined.

The β-hCG MAIAclone kit (Polymedco Inc. Cortlandt Manor, N.Y.), based on an immunoradiometric system, was used for quantitative determination of urinary β-hCG. Fifty µl of mouse urine samples diluted to achieve a final β-hCG concentration of 2.5–20 mIU/ml, standards, positive and negative controls were mixed with 0.5 ml of $^{125}$I anti-hCG antibodies in 12×75 mm glass tubes (VWR Scientific, Boston, Mass.) and incubated at 37° C. for 15 min. Two hundred µl of the magnetic separation matrix provided with the kit was then added to each tube and incubated for 5 min at room temperature. The magnetic reagent with bound β-hCG was separated using a magnetic concentrator (Polymedco Inc.). The matrix was washed in 0.5 ml of the MAIAclone washing buffer provided with the kit and reseparated magnetically. The radioactivity of each sample was analyzed in a Gamma 5500 counter (Beckman, Fullerton, Calif.). The minimal detectable level of β-hCG was 2.5 mIU/ml. Urinary β-hCG levels were normalized to urinary creatinine measured with a Roche Hitachi 917 analyzer (Roche Diagnostics, Indianapolis, Ind.). The ratio of β-hCG to creatinine was expressed as mIU β-hCG/mg creatinine.

CG tumors injected into mice resulted in the appearance of β-hCG in the serum. To determine whether β-hCG would be excreted in the urine of mice, as it is in pregnant women, the concentrations of β-hCG in urine and serum of mice with subcutaneous B16-CG tumors were compared. There was a tight correlation between the urine and serum concentrations, with the urine concentration equal to 3.8±0.31 times the serum concentration. This ~four-fold concentration of β-hCG in the urine was linear over a wide range of serum concentrations, ranging from 10–240 mIU/ml in the six mice assayed. The levels of urinary β-hCG in individual mice were reproducible when urine samples were collected at different time periods during a single day.

To assess the relationship between β-hCG levels and tumor weights, tumors in nude mice were completely excised and weighed immediately following urine collections. To determine the minimal tumors in mice that yielded positive urinary β-hCG, B16-CG cells were intravenously injected into five C57BL/6 mice ($10^5$ cells/mouse) and subcutaneously injected into five nude mice ($10^6$ cells/mouse). Lung weights were compared using the two-tailed Student's t test.

EXAMPLE 4
Urinary Levels of β-hCG in Tumor-Bearing Mice and Tumor Histology

To evaluate the utility of the CG system, mouse tumors were established at several sites, including the lungs, spleen, peritoneum, and skin, as previously described. All mice with tumors secreted β-hCG into their urine, while no β-hCG was found in the urine of mice without tumors, documenting the specificity of the assay. Urinary β-hCG could be detected two days after subcutaneous injection of $3\times10^6$ B 16-CG cells, one day following intraperitoneal injection of $2\times10^6$ EMT6-CG cells, seven days after intravenous injection of $1\times10^5$ B16-CG cells, and four days after intrasplenic injection of $1\times10^6$ B16-CG cells. Once detected, the β-hCG levels continued to rise until the animals became moribund (FIGS. 3A–3D). In addition to these syngeneic models, urinary β-hCG could be readily detected after injection of human SW480-CG cells into the skin or peritoneum of nude mice (described below).

To confirm that the expression of β-hCG was maintained in tumors, needle biopsies were performed at days 7 and 14 and stained with a β-hCG antibody. More than 95% of tumor cells were positive for β-hCG at both times, while tumors composed of parental cells exhibited no staining or excretion of β-hCG into the urine.

Tumors were biopsied with 25 gauge needles and tumor cells cultured in 48-well plates for four hours, allowing adherence to the surface. They were fixed in 3% paraformaldehyde in PBS at room temperature for 8 min, permeabilized with 0.3% NP-40 in PBS for 8 min., then washed in PBS and incubated with a primary mouse anti-β-hCG monoclonal antibody (Biogenex, San Ramon, Calif.) at 1:100 dilution. After incubation at room temperature for 1 hour, cells were washed and developed with an avidin-biotin complex peroxidase method (Biogenex). Immunoreactivity was detected using the 3,3'-diaminobenzidine chromagen (Sigma, St. Louis, Mo.). For histologic examination, the organs or tumors of mice were formalin-fixed, paraffin-embedded, and processed for routine hematoxylin and eosin staining.

EXAMPLE 5
Quantitation of Tumor Burdens

Figure 4A:
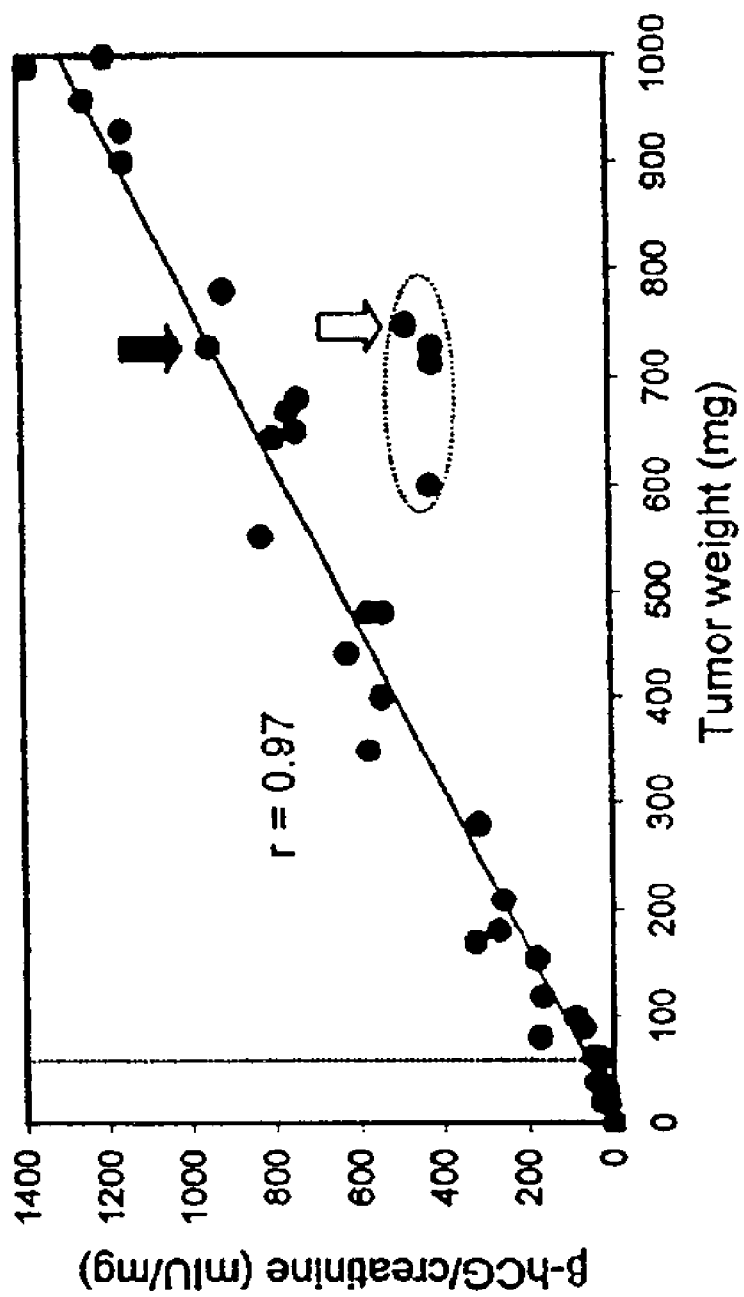
FIG. 4A. Relationship between urinary β-hCG levels and tumor weights. The solid line represents a simple linear regression between urinary β-hCG levels and the weights of subcutaneous B16-CG tumors. Each dot represents one tumor resected from an individual mouse. The dots to the left of the vertical line represent occult tumors which were barely visible or palpable, so the weights shown for these tumors are only approximate. The tumors represented by dots within the circle all had substantial necrosis.
Figure 4B:
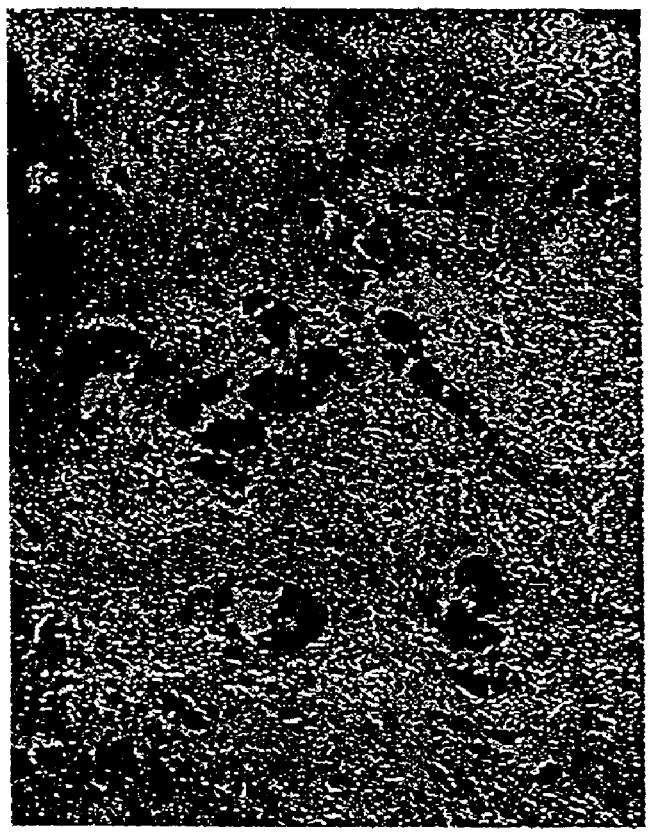
FIG. 4B. Relationship between urinary β-hCG levels and tumor weights. Hematoxylin and eosin stained sections of representative tumors. The tumor depicted on the right (corresponding to open arrow in FIG. 4A) exhibited extensive necrosis at its center. The tumor depicted on the left (corresponding to closed arrow in FIG. 4A) demonstrated viable tumor cells throughout.
Figure 4B:
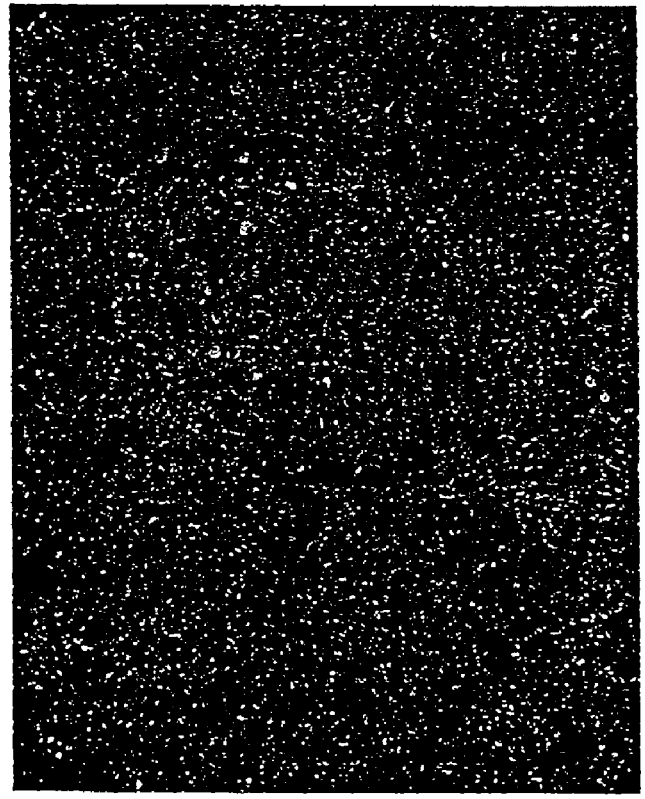

To determine the relationship between tumor load and urinary β-hCG levels, urine was collected from 37 animals with subcutaneous B16-CG tumors of various sizes. In each animal, the tumor was cleanly and completely excised within a few hours of urine collection and weighed. As shown in FIG. 4A, there was a striking linear relationship between urinary β-hCG levels and tumor weights (regression coefficient of 0.97, p<0.001). There were only four tumors in which urinary β-hCG levels and tumor weights were discordant (circled in FIG. 4A). Histologic examination of all tumors showed minimal tumor necrosis except for the four tumors with discordant urinary β-hCG levels and tumor weights (FIG. 4B). These four tumors each contained substantial necrosis in their central regions (FIG. 4B).

Next, the minimal size of tumors that could be detected with the CG system was determined. Urinary β-hCG could be detected (β-hCG level>2.5 mIU/ml) even when there were no grossly visible or palpable tumor nodules in the skin, lungs, or peritoneum after subcutaneous, intravenous, or intraperitoneal injections, respectively. The lungs from the mice receiving intravenous injections of B16-H10 cells were examined histologically immediately after urinary β-hCG could first be detected. Only three to five microscopic tumors, each containing 10 to 100 cells, could be found in standard sections ($6\mu\times0.5$ $cm^2$). There was no difference between the total lung weights of normal animals (169±6.5 mg) and those with minimal tumors detectable with the CG system (172±5.2 mg). Urinary β-hCG could be also detected in mice injected intraperitoneally with EMT6-H1 cells even in the absence of ascites or tumor implants in the peritoneum. All mice with clinically occult tumors, detectable only through the measurement of urinary β-hCG, appeared active and healthy.

EXAMPLE 6
Monitoring Therapy with the Recombinant Tumor Cell System

Figure 5A:
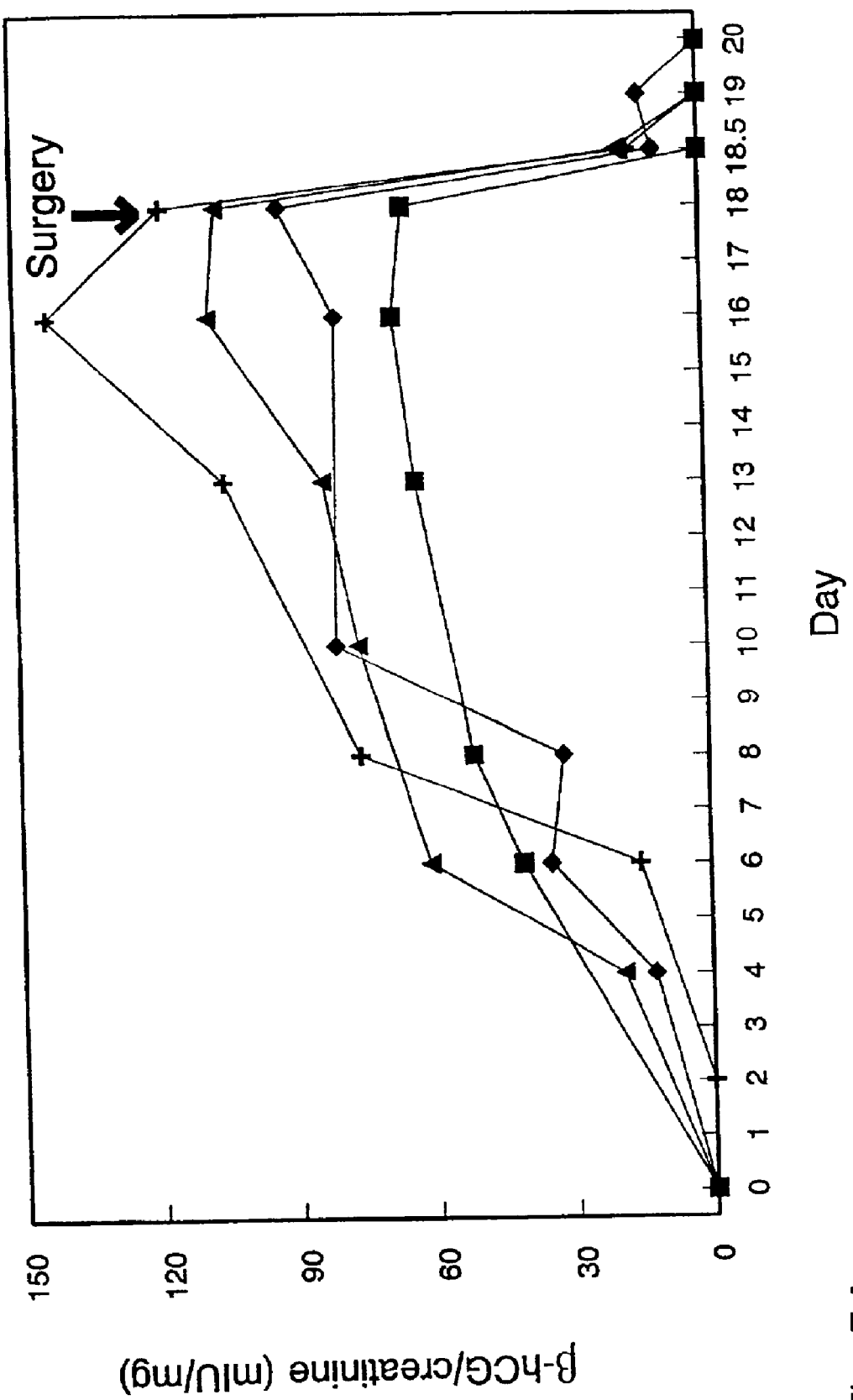
FIG. 5A. β-hCG levels after therapy. Urinary β-hCG levels before and after surgical removal of subcutaneous SW480-CG tumors. The β-hCG levels progressively increased as the tumors enlarged, but rapidly decreased after tumor excision at day 18 (arrow).
Figure 5B:
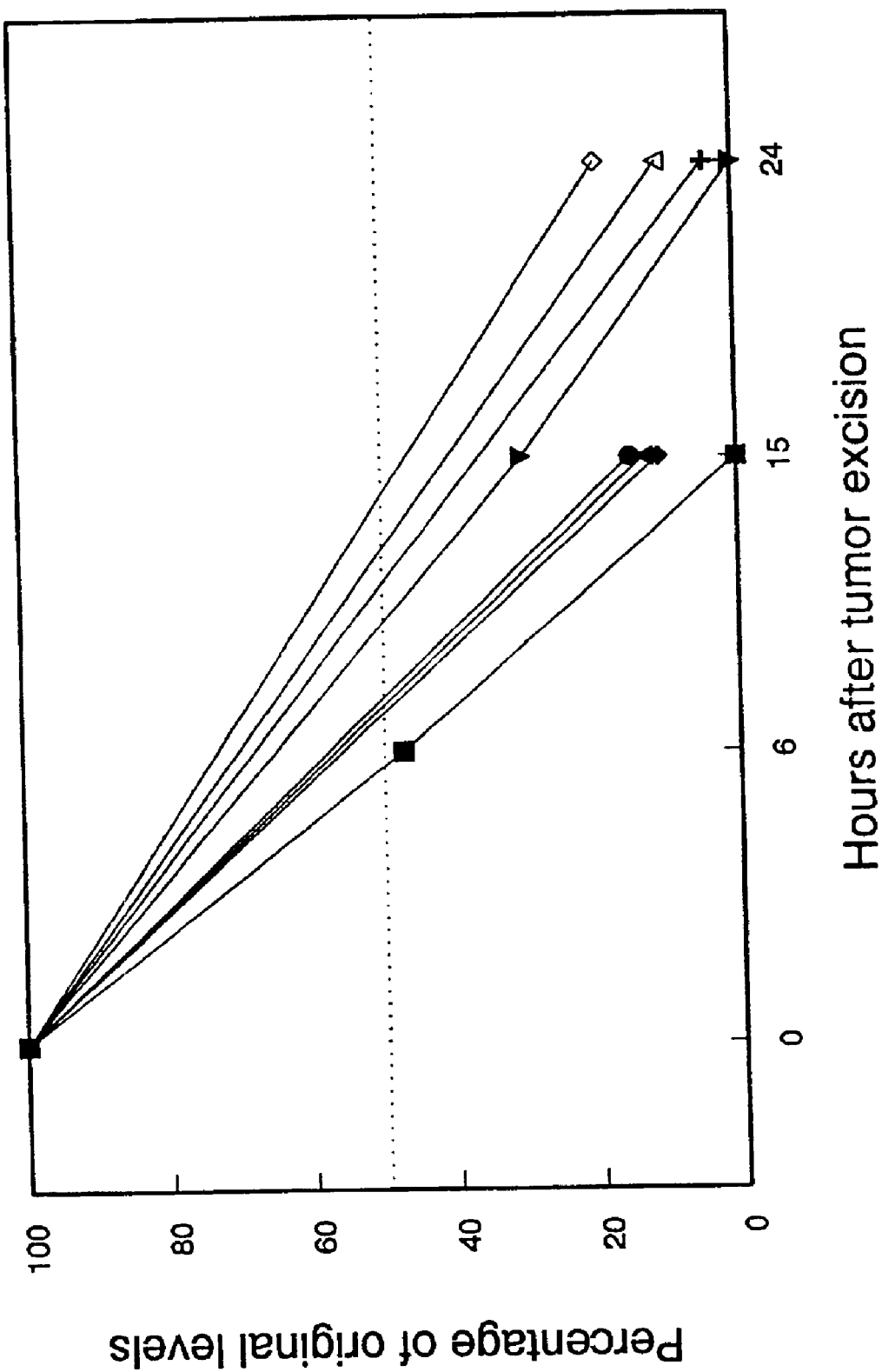
FIG. 5B. Kinetics of urinary β-hCG levels following surgical removal of SW480-CG tumors from eight different mice.

The recombinant tumor system of the present invention permits researchers to follow the growth of internal tumors after experimental therapeutics without sacrificing the animals. The use of the recombinant tumors for such applications obviously depends on a relatively rapid clearance of β-hCG following removal or death of tumor cells. To evaluate the half-life of β-hCG, subcutaneous SW480-CG tumors were surgically removed 18 days after implantation. Urinary β-hCG levels rapidly dropped to undetectable levels within a day or two of their removal (FIG. 5A). More detailed examinations in eight animals showed that the half-life of urinary β-hCG was 11±2.3 hours (FIG. 5B).

Next the recombinant tumor system of the present invention was applied to a chemotherapeutic model. EMT6-CG cells were transfected with a vector encoding herpes simplex virus thymidine kinase, making them sensitive to ganciclovir. EMT6-CG-TK cells were injected intraperitoneally, and mice were treated with ganciclovir after three days, a time when no clinical symptoms or ascites were apparent but when all mice exhibited detectable levels of urinary β-hCG. Urinary β-hCG levels continued to increase for one day after the initiation of ganciclovir treatment, but then declined to background levels over the next five days (FIG. 5C). Necropsy at this time revealed that the mice were apparently tumor free, without ascites or peritoneal implants. The difference between the kinetics of tumor cell death mediated by surgery and chemotherapy is readily evident through comparison of FIGS. 5A and 5C. Control EMT6-CG tumors treated with ganciclovir continued to grow, as indicated by high levels of urinary β-hCG and eventual clinical symptoms (FIG. 5C).

References

1. Williams, N. N. et al. Growth-factor-independence and invasive properties of colorectal carcinoma cells. *Int J Cancer* 50, 274–80 (1992).
2. Kerbel, R. S. What is the optimal rodent model for anti-tumor drug testing?*Cancer Metastasis Rev* 17, 301–4 (1998).
3. Staroselsky, A. N. et al. The use of molecular genetic markers to demonstrate the effect of organ environment on clonal dominance in a human renal-cell carcinoma grown in nude mice. *Int J Cancer* 51, 130–8 (1992).
4. Fidler, I. J., Wilmanns, C., Straroselsky, A., Dong, Z. & Fan, D. Modulation of tumor cell response to chemotherapy by the organ environment. *Cancer Metastasis Rev* 13, 209–222 (1994).
5. Killion, J. J., Radinsky, R. & Fidler, I. J. Orthotopic models are necessary to predict therapy of transplantable tumors in mice. Cancer Metastasis Rev 17, 279–84 (1998).
6. Wilmanns, C., Fan, D., O'Brian, C. A., Bucana, C. D. & Fidler, I. J. Orthotopic and ectopic organ environments differentially influence the sensitivity of murine colon carcinoma cells to doxorubicin and 5-fluorouracil. *Int J Cancer* 52, 98–104 (1992).
7. Dong, Z. et al. Organ-specific modulation of steady-state mdr gene expression and drug resistance in murine colon cancer cells. *J Natl Cancer Inst* 86, 913–920 (1994).
8. MacLaren, D. C. et al. Repetitive, non-invasive imaging of the dopamine D2 receptor as a reporter gene in living animals. *Gene Therapy* 6, 785–791 (1999).
9. Galons, J. -P., Altbach, M. I., Paine-Murrieta, G. D., Taylor, C. W. & Gillies, R. J. Early increases in breast tumor xenograft water mobility in response to paclitaxel therapy detected by non-invasive diffusion magnetic resonance imaging. *Neoplasia* 1, 113–117 (1999).
10. Stegman, L. D. et al. Noninvasive quantitation of cytosine deaminase transgene expression in human tumor xenografts with in vivo magnetic resonance spectroscopy. *Proc Natl Acad Sci USA* 96, 9821–6 (1999).
11. Jacobs, A. et al. Functional coexpression of HSV-1 thymidine kinase and green fluorescent protein: implications for noninvasive imaging of transgene expression. *Neoplasia* 1, 154–161 (1999).
12. Cole, L. A. hCG, its free subunits and its metabolites. Roles in pregnancy and trophoblastic disease. *J Reprod Med* 43, 3–10 (1998).
13. Wu, A. H., Wong, S. S., Waldron, C. & Chan, D. W. Automated quantification of choriogonadotropin: analytical correlation between serum and urine with creatinine correction. *Clin Chem* 33, 1424–6 (1987).
14. Shih, I. -M., Mazur, M. T. & Kurman, R. J. in *Diagnostic Surgical Pathology* (ed. Sternberg, S. S.) 2067–2086 (Williams & Wilkins Publishers, New York, 1999).
15. Kanazawa, K. et al. Establishment and characterization of a subline predisposed to pulmonary metastasis from a human gestational choriocarcinoma cell line in nude mice. *Acta Obstet Gynecol Scand* 68, 429–34 (1989).
16. Takahashi, Y., Ueno, M. & Mai, M. Establishment of a human chorionic gonadotropin-producing human gastric carcinoma in nude mice. *J Surg Oncol* 48, 96–100 (1991).
17. Newman, D. J. & Price, C. P. in *Tietz Textbook of Clinical Chemistry* (eds. Burtis, C. A. & Ashwood, E. R.) 1204–1270 (W.B. Saunders Co., Philadelphia, 1999).
18. Culver, K. W. et al. In vivo gene transfer with retroviral vector-producer cells for treatment of experimental brain tumors. *Science* 256, 1550–2 (1992).
19. Caruso, M. et al. Regression of established macroscopic liver metastases after in situ transduction of a suicide gene. *Proc Natl Acad Sci USA* 90, 7024–8 (1993).
20. Pesce, A. J., Bubel, H. C., DiPersio, L. & Michael, J. G. Human lactic dehydrogenase as a marker for human tumor cells grown in athymic mice. *Cancer Res* 37, 1998–2003 (1977).
21. DiPersio, L., Kyriazis, A. P., Michael, J. G. & Pesce, A. J. Monitoring the therapy of human tumor xenografts in nude mice by the use of lactate dehydrogenase. *J Natl Cancer Inst* 62, 375–9 (1979).
22. Marini, F. C., 3rd, Nelson, J. A. & Lapeyre, J. N. Assessment of bystander effect potency produced by intratumoral implantation of HSVtk-expressing cells using surrogate marker secretion to monitor tumor growth kinetics. *Gene Ther* 2, 655–9 (1995).
23. Kim, N. S., Kim S. J., Lee, G. M. Clonal variability within dihydrofolate reductase-mediated gene amplified Chinese hamster ovary cells: stability in the absence of selective pressure. *Biotechnol Bioeng* 20:679–88 (1998).
24. Rattle, S. J., Purnell, D. R., Williams, P. I., Siddle, K. & Forrest, G. C. New separation method for monoclonal immunoradiometric assays and its application to assays for thyrotropin and human choriogonadotropin. *Clin Chem* 30, 1457–61 (1984).

We claim:

1. A method for monitoring growth of tumor cells within an animal body, comprising:
   administering a recombinant tumor cell to an animal, wherein the recombinant tumor cell comprises an expression construct encoding a secretable exogenous marker protein;
   collecting urine from the animal;
   measuring the secretable exogenous marker protein in the urine, wherein the secretable exogenous marker protein in the urine is proportional to the number of viable tumor cells in the animal.

2. The method of claim 1 wherein repeated steps of collecting and measuring are performed at time intervals.

3. The method of claim 1 wherein the animal is treated with a therapeutic agent or a potential therapeutic agent before the step of administering.

4. The method of claim 1 wherein the animal is treated with a therapeutic agent or a potential therapeutic agent after the step of administering.

5. The method of claim 1 wherein the recombinant tumor cells are administered subcutaneously.

6. The method of claim 1 wherein the recombinant tumor cells are administered intraperitoneally.

7. The method of claim 1 wherein the recombinant tumor cells are administered intravenously.

8. The method of claim 1 wherein the recombinant tumor cells are administered intrasplenically.

9. The method of claim 1 wherein the recombinant tumor cells are administered intracranially.

10. The method of claim 1 wherein the recombinant tumor cells are administered under the renal capsule.

11. The method of claim 1 wherein the recombinant tumor cells are administered directly into the bowel wall.

12. The method of claim 1 wherein the recombinant tumor cells are administered intra-bladder.

13. The method of claim 1 wherein the recombinant tumor cells are not trophoblastic tumor cells.

14. The method of claim 1 wherein the animals are athymic.

15. The method of claim 1 wherein creatinine in the urine is also measured and the ratio of the secretable exogenous marker protein to creatinine is calculated.

16. The method of claim 1 wherein the tumor cells are syngeneic relative to the animal.

17. The method of claim 1 wherein the tumor cells are xenogeneic relative to the animal.

18. The method of claim 1 wherein the recombinant tumor cells constitutively express the secretable exogenous marker protein.

\* \* \* \* \*